United States Patent [19]

Ivanov et al.

[11] Patent Number: 4,705,876

[45] Date of Patent: Nov. 10, 1987

[54] PROCESS FOR PREPARING POWDER-LIKE IRON-SODIUM TARTRATE COMPLEX

[75] Inventors: Mikhail A. Ivanov; Jury A. Komkov; Vera V. Fomina, all of Leningrad, U.S.S.R.

[73] Assignee: Vsesojuznoe Nauchno-Proizvodstvennoe Obiedinenie Tselljuloznobumazhnoy Promyshlennosti, Leningrad, U.S.S.R.

[21] Appl. No.: 816,202

[22] Filed: Jan. 6, 1986

[51] Int. Cl.$^4$ .............................................. C07F 15/02
[52] U.S. Cl. ....................................................... 556/149
[58] Field of Search ......................................... 556/149

[56] References Cited

U.S. PATENT DOCUMENTS

| | | | |
|---|---|---|---|
| 1,964,696 | 6/1934 | Traube et al. | 556/146 X |
| 2,097,235 | 10/1937 | Schmidt et al. | 556/149 X |
| 2,474,989 | 7/1949 | Schnider | 556/149 X |
| 2,890,233 | 6/1959 | Opfermann | 559/149 |
| 3,200,136 | 8/1965 | Grossmith | 559/149 X |
| 3,553,316 | 1/1971 | Rubino | 556/149 X |
| 3,974,197 | 8/1976 | Parliment | 556/149 |
| 4,001,288 | 1/1977 | Gable et al. | 556/149 X |
| 4,265,675 | 5/1981 | Tsao et al. | 435/99 X |

*Primary Examiner*—Helen M. S. Sneed
*Attorney, Agent, or Firm*—Burgess, Ryan and Wayne

[57] ABSTRACT

A process for preparing a powder-like iron-sodium tartrate complex useful for the preparation of a solvent for cellulose which comprises reacting a salt of trivalent iron with sodium tartrate or primary sodium tartrate or a mixture thereof in an aqueous medium at a molar ratio of said reactants of 1:3.0–3.3 respectively, a concentration of the salt of trivalent iron of 0.5–0.7 mole/l of the starting reaction mixture and at a pH of the reaction mixture of 0.8–5.5 with the formation of a reaction mass containing the desired product; the latter is precipitated from the reaction mass by means of a precipitation agent such as methanol, ethanol, propanol or acetone at a volume ratio of the precipitation agent to the reaction mass of 0.7–1.5:1.0 respectively with the formation of a precipitate of the desired product and a mother liquor; the precipitate of the desired product is separated from the mother liquor and dried at a temperature of from 30° to 105° C.

6 Claims, No Drawings

PROCESS FOR PREPARING POWDER-LIKE IRON-SODIUM TARTRATE COMPLEX

FIELD OF THE INVENTION

The present invention relates to the pulp-and-paper and chemical industry, more specifically to processes for preparing a powder-like iron-sodium tartrate complex. This powder-like iron-sodium tartrate complex is employed for the preparation of a solvent for cellulose which comprises an aqueous alkaline solution of the above-mentioned complex. The cellulose solution in this solvent can be used for the determination of such characteristics as dynamic viscosity, intrinsic viscosity, degree of polymerization, molecular-weight distribution. Furthermore, the cellulose solvent prepared on the basis of the above-specified complex can be useful in various processes comprising treatment of cellulose and cellulose-containing materials.

BACKGROUND OF THE INVENTION

Known in the art is a process for producing a powder-like iron-sodium tartrate complex comprising reacting ferric chloride $FeCl_3$ with sodium tartrate $Na_2C_4H_4O_6$ in an aqueous medium at a molar ratio of the components of 1:3.0–3.5 respectively, a concentration of the ferric salt of 0.1 to 0.4 mol per liter of the starting reaction mixture and a pH of the reaction mixture about 14.2; the reaction is carried out in the presence of a stabilizing agent—sodium sulphite, glucose, galactose or hydrazine. Then from the resulting reaction mass the desired product is precipitated by means of a settling agent such as methanol, ethanol, butanol or acetone at a volume ratio of the settling agent to the reaction mass of 0.25–5.0:1.0 respectively. However, the stabilization agent and sodium chloride forming in the course of the reaction of sodium tartrate with ferric chloride are precipitated along with the desired product, wherefore the latter is contaminated.

Then the desired product together with the impurities is separated from the mother liquor and dried to give a powder-like iron-sodium tartrate complex of a green colour which contains the above-mentioned impurities (cf. U.S. Pat. No. 4,265,675 Int. Cl. C 13 K 1/02).

This prior art process has an essential disadvantage residing in that the resulting desired product contains the above-mentioned impurities. As it is well known, the presence of such impurities in the iron-sodium tartrate complex considerably lowers the dissolving power of an aqueous-alkaline solution of this complex in respect to cellulose. For this reason, the cellulose solvent obtained with the use of the powder-like iron-sodium tartrate complex prepared by the above-discussed process is less effective, since dissolution of cellulose therein is very slow (more than 24 hours) and incomplete. Such solvent cannot be used for analysis of the above-mentioned characteristics of cellulose.

Also known in the art is a process for preparing a powder-like iron-sodium tartrate complex comprising reacting ferric nitrate $Fe(NO_3)_3$ with sodium tartrate $Na_2C_4H_4O_6$ in an aqueous medium at the molar ratio of the above-mentioned reactants of 1.0:3.0 respectively, concentration of the ferric salt of 0.5–0.7 mole per liter of the starting reaction mixture and at a pH thereof having value equal to or exceeding 11. The desired product is precipitated from the reaction mass by ethanol at a volume ratio of the precipitation agent to the reaction mass equal to 1.0–3.0:1 respectively. In doing so, an impurity of sodium nitrate formed as a result of interaction of the starting components is precipitated together with the desired product. The precipitate comprising the desired complex and the impurity of sodium nitrate is in the form of a viscous oily liquid of a green colour. Then the green viscous oily liquid is separated from the mother liquor, whereafter the impurity of sodium nitrate is partially separated from this oily liquid. To this end, the liquid is diluted with water in the ratio of ⅓ volume of water per one volume of the oily liquid. The diluted oily liquid is treated with ethanol in the proportions specified hereinbefore. As a result, a residue is again obtained in the form of a green-colour viscous oily liquid, but with a smaller content of sodium nitrate. The abovementioned operations of dilution of the oily liquid with water, treatment with ethanol and separation of the precipitate from the mother liquor are repeated for two more times. This results in partial removal of the sodium nitrate impurity from the viscous oily liquid, the impurity passing into the mother liquor. Then water is removed from the oily liquid by way of a repeated treatment thereof with ethanol. As water is progressively removed from the oily liquid, the latter transforms into a glass-like product wherefrom a further removal of water by treatment with ethanol becomes substantially hindered. For this reason, the glass-like product is dried over $P_2O_5$ under vacuum. After drying the product is finely divided to give a pure particulated green iron-sodium tartrate complex (cf. Reyon Zellwole und andere Chemiefasern, Nr. 1, published January 1956 (Offizielles Organ der internationalen Chemiefaservereinigung, Berlin), Georg Jayme, Werner Bergmann "Über die vereinfachte Herstellung eines Lösungmittels für Zellulose auf der Basis eines Eisen-Weinsäure-Natrium Komplexes," s. 27–29).

A disadvantage of this prior art process resides in that it involves too many stages. Furthermore, this process necessitates the use of vacuum, $P_2O_5$ and high rates of ethanol consumption—30–40 ml of ethanol per gram of iron-sodium tartrate complex. The yield of the desired product in this process is only 75% of the theoretical. The desired product prepared by this process is hygroscopic and requires special storage conditions. The process does not make it possible to prepare a complex of iron with sodium tartrate which would have a reproducible composition, since the above-mentioned water washing employed for the removal of the impurity of sodium nitrate from the oily liquid results in a partial (with different degree) hydrolysis of iron.

The process is hardly implementable, it is impossible to be performed on a commercial scale.

SUMMARY OF THE INVENTION

It is an object of the present invention to provide such a process for preparing a powder-like iron-sodium tartrate complex which would make it possible to obtain the desired product of a high-purity grade.

It is another object of the present invention to provide such a process for preparing a powder-like iron-sodium tartrate complex which would make it possible to obtain the desired product in a high yield.

It is still another object of the present invention to provide a process which would feature a simple technology and equipment employed.

These objects are accomplished by the provision of a process for preparing a powder-like iron-sodium tartrate complex comprising interaction of a salt of a trivalent iron with sodium tartrate or primary sodium tartrate or a mixture thereof in an aqueous medium at a molar ratio of the reactants of 1:3.0–3.3 respectively and at a concentration of the salt of trivalent iron of 0.5–0.7 mole per liter of the starting reaction mixture with the formation of a reaction mass containing the desired product, precipitation of the desired product from the reaction mass by means of a precipitation agent such as methanol, ethanol or propanol, or acetone at a molar ratio of the precipitation agent to the reaction mass equal to 0.7–1.5:1.0 respectively, with the formation of a precipitate of the desired product and of a mother liquor; separation of the desired product precipitate from the mother liquor and drying, wherein in accordance with the present invention the interaction between the reactants is effected at a pH of the starting reaction mixture equal to 0.8–5.5 and the drying of the desired product precipitate is carried out at a temperature within the range of from 30° to 105° C.

The process according to the present invention makes it possible to obtain the desired product with a high purity grade (the content of impurities does not exceed 3.0%) and a high yield (up to 92–95% of the theoretical as calculated for the starting salt of trivalent iron); the product is also non-hydroscopic. The process is simple as to its procedure and the equipment employed; it involves a small number of operations and can be readily implemented on a commercial scale. Furthermore, the process of the present invention makes it possible to considerably (by nearly 15 times) reduce the rate of consumption of the precipitation agent, to eliminate the use of vacuum and $P_2O_5$.

These advantages of the process according to the present invention are due to the fact that the interaction of a salt of trivalent iron (for example, chloride, nitrate, perchlorate or acetate thereof) with sodium tartrate or primary sodium tartrate or a mixture thereof is effected at a pH of the starting reaction mixture of 0.8 to 5.5. The reaction mass formed under these conditions comprises a yellow colloidal solution containing the desired product and the impurity in the form of a salt of sodium (i.e. sodium chloride, nitrate, perchlorate or acetate) forming as a result of the interaction of the initial reactants. Upon introduction of a precipitation agent into the reaction mass mentioned hereinabove a precipitate of the desired product is formed in the form of a finely-divided yellow solid phase and a mother liquor. During precipitation of the desired product this impurity (sodium salt) passes into the mother liquor. The desired product precipitate can be readily separated from the mother liquor containing the contaminating sodium salt. Water can be readily removed from the desired product precipitate recovered from the mother liquor by drying at a temperature within the range of from 30° to 105° C. without applying vacuum or using special drying agents (such as $P_2O_5$). As a result, the desired product is obtained in the form of a yellow powder necessitating no additional disintegration.

The aqueous alkaline solution of the powder-like iron-sodium tartrate complex produced by the process according to the present invention is a highly-effective solvent for cellulose of different nature (for example, wood or cotton cellulose). Cellulose dissolves rather rapidly in this solvent (within 20–30 minutes) and completely which makes it possible to use this solvent in the determination of such characteristics of cellulose as dynamic viscosity, intrinsic viscosity, degree of polymerization, molecular mass distribution.

As it has been already mentioned hereinbefore, the reaction of a salt of trivalent iron with sodium tartrate or primary sodium tartrate or a mixture thereof is carried out at a molar ratio thereof of 1.0:3.0–3.3 respectively. It is inadvisable to use the above-mentioned reactants at a molar ratio thereof above 1.0:3.0, since the lowering of the amount of sodium tartrates relative to the amount of the ferric salt results in the formation of a reaction mass containing, in addition to the desired product, iron hydroxide as well. The latter is precipitated as an impurity together with the desired product and does not pass into the mother liquor. The presence of ferric hydroxide in the desired product impairs quality of the solvent for cellulose prepared on the basis of the desired product. It is inadvisable to use the above-mentioned reactants at their molar ratio of less than 1.0:3.3 for the following reasons. At a ratio below the above-specified value the amount of sodium tartrate becomes increased relative to the ferric salt, wherefore the salt of tartaric acid is not fully reacted with the ferric salt. The excessive unreacted sodium tartrate remains in the desired product as an impurity due to its poor solubility in alcohols and acetone. Then this impurity passes into the cellulose solvent prepared on the basis of the desired product. However, it is known that the best dissolving capacity in respect of cellulose is inherent in aqueous-alkaline solutions of iron-sodium tartrate complexes with a molar ratio of iron: tartrate equal to 1.0:3.0–3.3 respectively. The presence of an excessive amount of sodium tartrate in these solutions lowers their dissolving capacity relative to cellulose. Furthermore, the excess of sodium tartrate in the cellulose solvent brings about an unreasonably high consumption of this valuable reagent.

An optimal concentration of a ferric salt at which this salt is reacted with sodium tartrate or primary sodium tartrate or with a mixture thereof is within the range of from 0.5 to 0.7 mol per liter of the starting reaction mixture. It is inadvisable to lower the content of the ferric salt below 0.5 mole/l, since this is connected with an increasing content of water in the formed reaction mass. In this case, to retain a high yield of the desired product, an unreasonably high rate of the precipitation agent consumption is required. It is not advisable to increase the ferric salt concentration above 0.7 mole/l since the content of water in the formed reaction mass becomes insufficient for a complete dissolution and removal, with the mother liquor, of the salt of sodium contained in the reaction mass as impurity.

It is undesirable to carry out the reaction of the starting components at a pH of the initial reaction mixture below 0.8, since at low pH values the amount of the precipitation agent required for settling-out of the desired product becomes sharply increased. It is also inexpedient to carry out the reaction at a pH of the initial reaction mixture above 5.5, since at higher pH values the desired product is settled in the form of an oily viscous liquid wherefrom the sodium salt impurity and water are difficult to remove.

The precipitation of the desired product from the formed reaction mass is effected at a volume ratio of the precipitation agent to the reaction mass equal to 0.7–1.5:1.0 respectively. It is inadvisable to lower this ratio below 0.7:1.0, since this results in a decreased yield of the desired product. Increasing the ratio above 1.5:1.0 causes an unreasonable over-consumption of the precipitation agent, since the yield of the desired product does not increase with a further increase of this ratio.

It is undesirable to dry the desired product at a temperature below 30° C., since with a lower temperature the drying period is considerably protracted. Temperatures above 105° C. are not advisable, since at such temperatures the iron-sodium tartrate complex is hydrolyzed and decomposed.

DETAILED DESCRIPTION OF THE INVENTION

The process for preparing a powder-like iron-sodium tartrate complex is performed in the following manner.

A salt of trivalent iron is charged into a reaction vessel. As the salt of trivalent iron ferric chloride, nitrate, perchlorate, acetate and other salts well-soluble in water can be used. The iron salt is introduced either as an aqueous solution or as a solid with a subsequent additon of water. Water is used in such amount that the entire quantity of the ferric salt be dissolved and its concentration in the starting reaction mixture be within the range of from 0.5 to 0.7 mole/l. Then the aqueous solution of the ferric salt is added with a calculated amount of sodium tartrate $Na_2C_4H_4O_6$ or primary sodium tartrate $NaC_4H_5O_6$ or a mixture thereof. Proportions of sodium salts of tartaric acid in their mixtures can be broadly varied. These salts of tartaric acid can be used as they are in the ready-to-use form, or can be prepared from tartaric acid which is introduced into an aqueous solution of a ferric salt and neutralized with sodium hydroxide.

The interaction of a salt of trivalent iron (ferric salt) with salts of tartaric acid or mixtures thereof is effected at room temperature and at pH value of the starting reaction mixture within the range of from 0.8 to 5.5. Depending on particular starting reactants and their molar proportions, to maintain pH values within the above-specified range use is made of sodium hydroxide, or tartaric acid.

The prepared starting reaction mixture is stirred for 5-15 minutes to give a yellow reaction mass containing the desired product. To this reaction mass is added with a precipitation agent such as methanol, ethanol or propanol, or acetone at a volume ratio of the precipitation agent to the reaction mass of 0.7-1.5:1.0 respectively. As a result, a precipitate of the desired product is obtained in the form of a yellow fine powder and a mother liquor. The precipitate is separated from the mother liquor, e.g. by filtration, and dried at a temperature of from 30° to 105° C. The resulting iron-sodium tartrate complex is obtained in the form of a yellow powder.

The powder-like iron-sodium tartrate complex produced by the process according to the present invention is used for the preparation of a solvent for cellulose. To this end, the complex is dissolved in an aqueo-alkaline solution at the pH of 14.2. Cellulose of different nature is rapidly (within 20-30 minutes) and completely dissolved in such solvent, wherefore it can be employed in the pulp-and-paper and chemical industries for determination of such characteristics of cellulose as dynamic viscosity, intrinsic viscosity, degree of polymerization and molecular-mass distribution.

For a better understanding of the present invention some specific examples illustrating its particular embodiments are given hereinbelow.

EXAMPLE 1

48 ml of a 0.62M aqueous solution of ferric chloride $FeCl_3$ and 21.8 g of sodium tartrate $Na_2C_4H_4O_6$ are charged into a reaction vessel (the molar ratio between the components is 1.0:3.15). The concentration of the ferric salt in the starting reaction mixture is 0.5 mole/l. The pH value of the starting reaction mixture is maintained at 5.5 by the addition of sodium hydroxide. The reaction mixture is stirred for 10-15 minutes. The reaction of the iron salt with sodium tartrate gives a reaction mass containing the desired product, i.e. iron-sodium tartrate complex. Then the reaction mass is added with 90 ml of a precipitation agent—ethanol (the volume ratio of the precipitation agent to the reaction mass is 1.5:1.0). As a result, a fine precipitate of the desired product and a mother liquor are obtained. The precipitate is separated from the mother liquor by filtration and dried at 35° C. to give 22 g of a powder-like yellow iron-sodium tartrate complex. The desired product yield is 93% of the theoretical value (as calculated for the starting salt of iron). The content of sodium chloride impurity in the desired product is 3.0%.

EXAMPLE 2

A powder-like iron-sodium tartrate complex is obtained by the procedure similar to that described in the foregoing Example 1. In the reaction 48 ml of a 0.62M aqueous solution of ferric nitrate $Fe(NO_3)_3$ and 21.8 g of sodium tartrate $Na_2C_4H_4O_6$ are employed (the molar ratio of the reactants is 1.0:3.15). The concentration of the iron salt in the initial reaction mixture is 0.5 mole/l. The pH value of the starting reaction mixture is maintained at 3.2 by the addition of sodium hydroxide. To precipitate the desired product from the reaction mass formed in the reaction of the starting reactants ethanol is used in the amount of 42 ml (the volume ratio of the precipitation agent to the reaction mass is 0.7:1.0). The precipitate of the desired product filtered-off from the mother liquor is dried in a drying cabinet at the temperature of 60° C. to give 20 g of a powder-like yellow iron-sodium tartrate complex. The desired product yield is 92% of the theoretical. The content of sodium nitrate impurity in the desired product is 2.5%.

EXAMPLE 3

A powder-like iron-sodium tartrate complex is prepared in a manner similar to that of Example 1 hereinbefore. 43 ml of a 0.7 M aqueous solution of ferric nitrate $Fe_2(NO_3)_3$ are reacted with 18.4 g of a mixture of sodium tartrate $Na_2C_4H_4O_6$ with primary sodium tartrate $NaC_4H_5O_6$ at the molar ratio of the salts of tartaric acid in their mixture of 1:4 respectively. The molar ratio of the ferric salt to the tartrates is equal to 1:3.1. The concentration of the ferric salt in the starting reaction mixture is 0.55 mole/l. The pH value of the starting reaction mixture is maintained at 3.1. by the addition of sodium hydroxide. To recover the desired product from the reaction mixture formed as a result of interaction of the starting reactants ethanol is used as a precipitation agent in the amount of 55 ml (the volume ratio of the precipitation agent to the reaction mass is 1.0:1.0). The precipitate of the desired product separated from the mother liquor by filtration is dried at the temperature of 105° C. to give 20.1 g of a powder-like iron-sodium tartrate complex. The yield of the desired product is 94% of the theoretical value. The content of sodium nitrate impurity in the desired product is 2.5%.

EXAMPLE 4

A powder-like iron-sodium tartrate complex is obtained in a manner similar to that described in Example 1 hereinbefore. 48 ml of a 0.62M aqueous solution of ferric chloride are reacted with 17.1 g of primary sodium tartrate $NaC_4H_5O_6$ (the molar ratio of the reactants is 1.0:3.0). The concentration of the iron salt in the starting reaction mixture is equal to 0.5 mole/l. The pH value of the starting reaction mixture is maintained at 0.8 by the addition of tartaric acid. To recover the desired product from the reaction mixture formed as a result of interaction of the starting components, propanol is used in the amount of 90 ml (the volume ratio of the precipitation agent to the reaction mass is 1.5:1.0). The precipitate of the desired product filtered from the mother liquor is dried at the temperature of 30° C. to give 17.2 g of a powder-like iron-sodium tartrate complex. The yield of the desired product is 92% of the theoretical value. The content of sodium chloride impurity in the desired product is 3%.

EXAMPLE 5

A powder-like iron-sodium tartrate complex is prepared in a manner similar to that of Example 1 using 30 ml of 1 M aqueous solution of ferric perchlorate $Fe(ClO_4)_3$ and 21.8 g of sodium tartrate $NaC_2H_4O_6$ (the molar ratio of the reactants is of 1.0:3.15). The concentration of the ferric salt in the starting reaction mixture is 0.7 mole/l. The pH value of the starting reaction mixture is maintained at 3.4 by the addition of sodium hydroxide. To precipitate the desired product from the reaction mass formed as a result of interaction of the starting components acetone is used in the amount of 65 ml (the volume ratio of the precipitation agent to the reaction mass is 1.5:1.0). The desired product precipitate separated from the mother liquor by filtration is dried at the temperature of 45° C. to give 20.6 g of a powder-like iron-sodium tartrate complex. The yield of the desired product is 95% of the theoretical. The content of sodium perchlorate impurity in the desired product is equal to 2.0%.

EXAMPLE 6

A powder-like iron-sodium tartrate complex is prepared in a manner similar to that described in Example 1 hereinbefore using 48 ml of a 0.62 M aqueous solution of ferric acetate $Fe(CH_3COO)_3$ and 22.8 g of sodium tartrate $Na_2C_4H_4O_6$ (the molar ratio of the reactants is 1.0:3.3). The concentration of the ferric salt in the starting reaction mixture is 0.5 mole/l. The pH value of the starting reaction mixture is maintained at 3.3 by the addition of sodium hydroxide. To precipitate the desired product from the reaction mass formed as a result of interaction of the starting reactants ethanol is used in the amount of 90 ml (the volume ratio of the precipitation agent to the reaction mass is 1.5:1.0). The drying of the desired product precipitate separated from the mother liquor by filtration is conducted at the temperature of 40° C. to give 21 g of a powder-like iron-sodium tartrate complex. The desired product yield is 92% of the theoretical value. The content of sodium acetate impurity in the desired product is 3%.

EXAMPLE 7

A powder-like iron-sodium tartrate complex is prepared in a manner similar to that described in Example 1 using 38 ml of a 0.79 M aqueous solution of ferric nitrate $Fe(NO_3)_3$ and 20.6 g of a mixture of sodium tartrate $Na_2C_4H_4O_6$ with primary sodium tartrate $NaC_4H_5O_6$ at the molar ratio of the tartrates in the mixture of 4:1 respectively. The molar ratio of the ferric salt to the tartrates is equal to 1:3.1. The concentration of the ferric salt in the starting reaction mixture is equal to 0.6 mole/l. The pH value of the starting reaction mixture is maintained at 3.1 by the addition of sodium hydroxide. To precipitate the desired product from the reaction mass formed as a result of interaction of the starting reactants methanol is used in the amount of 45 ml (the volume ratio of the precipitation agent to the reaction mass is 0.9:1.0). The drying of the desired product precipitate separated from the mother liquor by filtration is effected in a drying cabinet at 50° C. to give 20.3 g of a powder-like iron-sodium tartrate complex. The yield of the desired product is 95% of the theoretical. The content of sodium nitrate impurity in the desired product is equal to 3%.

Given hereinbelow is Example 8 illustrating the use of a powder-like iron-sodium tartrate complex prepared according to the procedure described in Example 2 hereinbefore for the preparation of a solvent for cellulose.

EXAMPLE 8

To 37.9 g of a powder-like iron-sodium tartrate complex prepared as in Example 2 60 ml of water are added and thoroughly intermixed. Then sodium hydroxide and water are added in such amounts as to obtain an aqueous-alkaline solution of the complex in the amount of 100 ml with a pH of about 14.2 which is a solvent for cellulose.

Into 50 ml of the prepared solvent 0.03 g of wood pulp obtained by the sulphite process is charged. A complete dissolution of the pulp is observed after stirring for 20 minutes.

The thus-prepared solution of cellulose is used for the determination of an intrinsic viscosity by the procedure described in the Internation Standard ISO No. 5351/2-1981 (E), p.3. The value of the intrinsic viscosity of the solution of cellulose as determined by this procedure is 700 ml/g.

What is claimed is:

1. A process for preparing a powder-like iron-sodium tartrate complex comprising reacting a salt of trivalent iron with at least one salt of tartaric acid selected from the group consisting of sodium tartrate and primary sodium tartrate and mixtures thereof in an aqueous medium at a molar ratio of said reactants of 1:3.0-3.3 respectively, a concentration of salt of trivalent iron of 0.5-0.7 mol/l of the starting reaction mixture and at a pH of the starting reaction mixture of from 0.8-5.5 to form a reaction mixture containing the iron-sodium tartrate complex; adding a precipitating agent to the reaction mixture to precipitate the iron-sodium tartrate complex from the reaction mixture to form a precipitated iron-sodium tartrate complex and an aqueous phase and recovering the precipitated iron-sodium tartrate complex.

2. The process of claim 1 which comprises adding a liquid precipitating agent to the reaction mixture in a volume ratio of precipitating agent to reaction mixture of from 0.7-1.5:1.

3. The process of claim 2 wherein the liquid precipitating agent is at least one member selected from the group consisting of methanol, ethanol, propanol, and acetone.

4. The process of claim 1 wherein the precipitated iron-sodium complex is recovered by separating the precipitate from the aqueous phase and drying the separated precipitate at a temperature of from 30° to 105° C.

5. The process of claim 2 wherein the precipitated iron-sodium complex is recovered by separating the precipitate from the aqueous phase and drying the separated precipitate at a temperature of from 30° to 105° C.

6. The process of claim 3 wherein the precipitated iron-sodium complex is recovered by separating the precipitate from the aqueous phase and drying the separated precipitate at a temperature of from 30° to 105° C.

* * * * *